United States Patent [19]
Reedy et al.

[11] 3,957,848
[45] May 18, 1976

[54] CYANOETHYLATION PROCESS

[75] Inventors: James D. Reedy, Williamstown; Paul H. Paugh, Sisterville, both of W. Va.

[73] Assignee: Union Carbide Corporation, New York, N.Y.

[22] Filed: Mar. 11, 1975

[21] Appl. No.: 557,246

[52] U.S. Cl.............................. 260/465.6; 260/464; 260/465 F
[51] Int. Cl.$^2$.............. C07C 120/00; C07C 121/38; C07C 121/30
[58] Field of Search.............. 260/465 F, 464, 465.6

[56] References Cited
UNITED STATES PATENTS

| | | | |
|---|---|---|---|
| 2,559,660 | 7/1951 | Rehberg | 260/465 F X |
| 2,818,422 | 12/1957 | Heininger | 260/465 F |
| 3,544,615 | 12/1970 | Poppelsdorf | 260/465 F |
| 3,560,549 | 2/1971 | Poppelsdorf | 260/465.6 X |

OTHER PUBLICATIONS

Organic Reactions, Vol. 5, 1949, p. 90.

*Primary Examiner*—Joseph P. Brust
*Attorney, Agent, or Firm*—Reynold J. Finnegan

[57] ABSTRACT

Cyanoethylation process for producing beta-cyanoethyl capped hydroxy compounds that are essentially free from polyacrylonitrile by-products.

5 Claims, No Drawings

CYANOETHYLATION PROCESS

BACKGROUND OF THE INVENTION

This invention relates to a process for cyanothylation of hydroxy compounds. More particularly, this invention relates to the production of beta-cyanoethyl capped hydroxy compounds that are essentially free of polyacrylonitrile by-products.

The production of beta-cyanoethyl capped hydroxy compounds by cyanoethylation is well known in the art and involves the addition reaction of an alcohol and acrylonitrile to form the corresponding beta-cyanoethyl capped alcohol (i.e., oxy nitrile) as exemplified by the following equation:

wherein R is an organic radical. The reaction proceeds rapidly and yields as high as about 97 percent can be obtained with certain alcohols. Strong bases, such as alkali metal alcoholates, oxides and hydroxides are the most common catalysts for effecting cyanoethylation (British Patent 544,421), although anion-exchange resins (U.S. Pat. No. 2,658,070) are also satisfactory catalysts.

However, one of the most serious drawbacks to cyanoethylation of alcohols in the presence of strong bases is the varying amounts of polyacrylonitrile byproduct formed as reported by J. Cason et al., *J. Org. Chem.*, 37, 1972 page 2577 (footnote No. 15) and M. J. Astle et al, *Industrial and Engineering Chemistry*, 44, 1952, page 2872. In addition to homopolymers of acrylonitrile, block copolymers of acrylonitrile may also be formed when strongly basic catalysts are used as reported in U.S. Pat. No. 3,544,615. In certain utility applications the presence of polyacrylonitrile or its block copolymers in the desired oxy nitrile product may be of no consequence. However, polyacrylonitrile or its block copolymers are poisons for many nobel metal catalysts such as nickel, palladium, platinum and the like. Thus, when it is desired to hydrogenate the oxy nitrile product to form primary amines the presence of polyacrylonitrile by-product is very troublesome. Similarly, the production of silicon-oxyalkylene nitrile compounds by platinum catalyzed hydrosilylation of a terminal olefin of an oxyalkylene nitrile (produced by cyanoethylation) in the presence of polyacrylonitrile contaminates proceeds slowly and incompletely. The problem is further aggravated in that prolonged contact of the silicon-oxyalkylene nitrile product with the poisoned platinum catalyst causes retrocyanoethylation and much of the acrylonitrile formed under these conditions will in turn form further polyacrylonitrile.

While the bulk of the polyacrylonitrile by-product cannot generally be successfully removed from a cyanoethylated alcohol by filtration or treatment with carbon black, it has been taught (U.S. Pat. No. 3,544,615) that polyacrylonitrile can be removed from certain cyanoethylated alcohols by employing a solvent that is miscible with the cyanoethylated product and immiscible with the polyacrylonitrile. However, such a purification process is an additional procedural step that must be carried out on the cyanoethylated alcohol product.

Thus, there is a clear need in the art for a cyanoethylated process that will produce beta-cyanoethyl capped hydroxy compound products that are already essentially free of polyacrylonitrile by-products, and which will eliminate the need for such purification procedures.

SUMMARY OF THE INVENTION

It has now been discovered that beta-cyanoethyl capped hydroxy compounds that are essentially free from polyacrylonitrile by-products can be prepared by reacting a hydroxy compound with acrylonitrile in the presence of water and a catalyst which is an alkali metal or tetraalkyl ammonium salt of an acid.

Accordingly, it is an object of this invention to provide a cyanoethylation process for producing betacyanoethyl capped hydroxy compounds that are essentially free from polyacrylonitrile by-products. Other objects and advantages of this invention will become readily apparent from the following description and appended claims.

More particularly the instant invention is directed to a cyanoethylation process for preparing beta-cyanoethyl capped hydroxy compounds that are essentially free of polyacrylonitrile by-products said process comprising reacting at a temperature of 0° to 80°C., a hydroxy compound selected from the group consisting of primary and secondary alcohols with acrylonitrile in the presence of water and a catalyst which is an alkali metal or tetraalkyl ammonium salt of an acid by (A) slowly adding said acrylonitrile to a mixture containing said hydroxy compound, water, and catalyst, (B) neutralizing said catalyst and recovering the beta-cyanoethyl capped hydroxy compound product; wherein:

a. said catalyst is soluble in said mixture of hydroxy compound, water and catalyst ingredients;
b. said acid has an aqueous pKa value of greater than 10 but less than 15;
c. the amount of catalyst employed is such that the aqueous pH of a separate mixture containing about 10 percent by weight of a sample of said mixture of hydroxy compound, water and catalyst ingredients and about 90 percent by weight of additional water ranges from about 9 to about 10.7;
d. the amount of acrylonitrile employed ranges from about 1 to about 1.1 moles for every hydroxy group on said hydroxy compound to be reacted;
e. the rate of contact between the hydroxy compound and acrylonitrile reactants is such that the reaction mixture of hydroxy compound, water, catalyst, and acrylonitrile never contains more than 5 percent by weight of unreacted acrylonitrile based on the total weight of said reaction mixture;
f. the amount of water employed ranges from about 0.1 to about 0.5 percent by weight based on the amount of said hydroxy compound employed.

DESCRIPTION OF THE PREFERRED EMBODIMENTS

As pointed out above, the hydroxy compounds that can be employed as starting materials in the process of this invention encompass any organic primary or secondary alcohol. Such compounds and/or methods for their preparation are well known in the art and include aliphatic alcohols, unsaturated aliphatic alcohols, polyether alcohols, polyhydric alcohols, and derivatives of the polyhydric alcohols which contain at least one hydroxy group. It has been further discovered that while the process of the instant invention works well with primary and secondary alcohols it works very poorly with tertiary alcohols. Among the more preferred hydroxy compound starting materials that may be mentioned are unsaturated polyether alcohols having the general formula $$H_2C = CH(CH_2)_yO(C_nH_{2n}O)_xH$$

wherein $y$ has a value of 0 to 4 inclusive, preferably 1, $n$ has a value of 2 to 4 inclusive, and $x$ has a value of 1 to 20 or higher, preferably 1 to 15. Such unsaturated polyether alcohols and/or methods for their preparation are well known in the art and are especially useful in the ultimate production of hydrolytically stable siloxane-oxyalkylene block copolymers.

Illustrative examples of such preferred unsaturated polyether alcohols include those compounds wherein the oxyalkylene units $(C_nH_{2n}O)_x$ can comprise oxyethylene units, $(-C_2H_4O-)$; oxypropylene units $(-C_3H_6O-)$; and oxybutylene units, $(-C_4H_8O-)$; as well as mixtures of such units, such as a mixture of oxyethylene and oxypropylene units. Of course, it is obvious that with regard to unsaturated polyether alcohols containing two or more different types of oxyalkylene units, that said units may be present in the compound in any random or nonrandom distribution order depending merely upon the desired final product of the process of the instant invention. Moreover, it is to be understood that while the hydroxy compound starting materials of this invention can be discrete chemical compounds, they may also be mixtures of various discrete species due at least in part to the manner in which they are made and while a single hydroxy compound can be employed as the starting material of this invention, mixtures of two or more different hydroxy compounds can also be employed if desired.

Illustrative of some of the more preferred hydroxy compounds are $$H_2C = CH-CH_2-OH$$

$$H_2C = CH-CH_2-O-(C_2H_4O)H$$

$$H_2C = CH-CH_2-O-(C_2H_4O)_{7.7}H$$

$$H_2C = CH-CH_2-O-(C_2H_4O)_{15}H$$

$$H_2C = CH-CH_2-O-(C_2H_4O)_nH$$

$$H_2C = CH-CH_2-O-(C_3H_6O)H$$

$$H_2C = CH-CH_2-O-(C_3H_6O)_4H$$

$$H_2C = CH-CH_2-O-(C_4H_8O)_xH$$

$$H_2C = CH-O-(C_2H_4O)H$$

$$H_2C = CH-(CH_2)_2-O-(C_2H_4O)H$$

$$H_2C = CH-(CH_2)_3-O-(C_3H_6O)H$$

$$H_2C = CH-(CH_2)_4-O-(C_4H_8O)H$$

$$H_2C = CH-CH_2-O-(C_2H_4O)(C_3H_6O)H$$

$$H_2C = CH-CH_2-O-(C_2H_4O)_2(C_3H_6O)H$$

and the like.

Of course, the acrylonitrile starting material employed in the cyanoethylation process of this invention is a known compound of the formula $H_2C = CHCN$. While the cyanoethylation process of this invention is obviously a stoichiometric reaction, the amount of acrylonitrile employed can range from about 1 to about 1.1 moles for every hydroxy group on the hydroxy compound starting material to be reacted to produce the desired cyanoethylated product. When yields above 90% by weight based on the amount of hydroxy compound employed are desired, it is preferred to employ a slight excess of acrylonitrile which excess may be removed by conventional stripping methods if desired after the catalyst has been neutralized. The use of higher excess amounts of acrylonitrile above the range given above should be avoided since such can lead to homopolymerization of the acrylonitrile to polyacrylonitrile.

Accordingly, it is obvious that the beta-cyanoethyl capped hydroxy compound products of this invention contain one or more oxynitrile radicals (i.e. $-OCH_2CH_2CN$), the number of said oxynitrile radicals merely being dependent upon the number of hydroxy groups on the hydroxy compound starting material to be reacted with acrylonitrile. The preferred beta-cyanoethyl capped hydroxy compound products are those having the general formula $H_2C = CH(CH_2)_yO(C_nH_{2n}O)_x CH_2CH_2CN$ wherein $n$, $x$, $y$ and the oxyalkylene units $(C_nH_{2n}O)_x$ are the same as defined above.

The catalyst employed in the process of this invention is an alkali metal or tetraalkyl ammonium salt of an acid (i.e., a proton donor), said acid having an aqueous pKa value of greater than 10 but less than 15. The aqueous pKa value of an acid is a conventional means for expressing the strength or degree of dissociation of said acid in an aqueous media, and may be determined by the conventional method of potentiometry as shown by *TITRATIONS IN NONAQUEOUS SOLVENTS* by W. Huber, p. 18, Acedemic Press, New York, N.Y. (1967).

The aqueous pKa value of the acid will determine the base strength of the corresponding alkali metal or tetraalkyl ammonium salt catalyst employed in the process of this invention. The use of acidic compounds having pKa values below or above the range given above will result in corresponding salt catalysts that are either too weak or too strong to achieve the desired optimum results of the process of this invention. Acidic compounds and/or methods for their preparation having pKa values in the range given above are known and include, e.g. methyl glycol, partial phosphate esters, cresols, partial pyrophosphate esters, and the like. Of course, it is to be understood that the use of acidic compounds that may promote side reactions, such as hydroperoxides, with the reactants involved should be avoided.

The amount of catalyst employed in the process of this invention will vary with the base strength of the catalyst employed and can be easily determined by routine experimentation. Thus, the amount of catalyst employed in the process of this invention must be such that the aqueous pH of a separate mixture containing about 10 percent by weight of a sample of a separate mixture of the hydroxy compound, water, and catalyst ingredients in the same proportions employed in the given process and about 90 percent by weight of additional water ranges from about 9 to about 10.7. Employing a catalyst concentration that will result in an aqueous pH outside of the range of about 9 to 10.7 as measured according to the above procedure can be detrimental to the process of the instant invention because at pH's below 9 the capping efficiency can decline to less than 80 percent and the reaction rates are prohibitively slow, while at pH values greater than about 10.7 polyacrylonitrile formation increases to the point where it becomes troublesome when attempting to run subsequent reactions as previously described.

Thus, suitable catalysts for the process of this invention and/or methods for their production are known and include the alkali metal or tetraalkyl ammonium salts of partial phosphate esters, alkyl mercaptans, cresols, partial pyrophosphate esters, and the like. Illustrative examples of said catalysts are such compounds as sodium or potassium salt of a partial phosphate ester such as GAFAC, (Product No. RS-610), or sodium di(2-ethylhexyl) phosphate or the sodium salt of p-cresol, tetramethyl-ammonium di(2-ethylhexyl) phosphate, and the like.

The preferred catalysts employed herein are the salts of partial phosphate esters such as those having the general formula

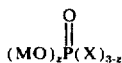

wherein M is an alkali metal or tetraalkyl ammonium radical; $z$ has a value of 1 to 2 inclusive and X is an alkoxy radical or a polyether radical of the formula $-(OC_nH_{2n})_xOR$ where R is a monovalent hydrocarbon radical e.g. alkyl, alkenyl and aryl radicals, the most preferred catalysts being the salts of partial phosphate esters having the general formula

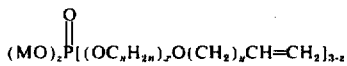

wherein M is an alkali metal, e.g. sodium or potassium and $n$, $z$, $x$, $y$ and the oxyalkylene units $(OC_nH_{2n})_x$ are the same as defined above. Of course, it is obvious and to be understood that while one may generally employ a single catalyst for a given process, if desired, mixtures of two or more different catalysts can be employed in the same process. Moreover, while the catalyst can be produced in the absence of the hydroxy compound used in the process invention, it is often desirable and convenient to produce said catalyst in the presence of said hydroxy compound and such is generally preferred when polyoxyalkylene alcohols are employed as the starting materials for the process of this invention.

The use of water in the process of this invention plays a supportive role in preventing the formation of polyacrylonitrile. The presence of a small amount of water in the process of this invention is necessary to achieve the optimum desired resuls and the amount of water employed can range from about 0.1 to about 0.5 weight percent, preferably about 0.3 weight percent, based on the amount of hydroxy compound starting material employed. Anhydrous conditions increase the likelyhood of forming undesirable polyacrylonitrile by-products, while too much water, e.g. greater than 1 percent by weight, can make the reaction prohibitively slow and result in poor yields.

The process of the instant invention is conveniently carried out by slowly adding acrylonitrile at a reaction temperature of 0°C. to 80°C., preferably about 15°C. to 60°C., to a solution mixture of the hydroxy compound, water and catalyst ingredients employed. Of course, it is to be understood that this addition encompasses the procedure of first charging said solution mixture to the reaction container and then adding the acrylonitrile as well as the less preferred procedure of simultaneously adding both said solution mixture and the acrylonitrile to the reaction container from separate charging tanks. Since acrylonitrile and an alcohol will normally react rapidly it is important to maintain the rate of contact between the hydroxy compound and acrylonitrile reactants in such a manner that the reaction mixture of all the ingredients of the process never contains more than about 5 percent by weight of unreacted acrylonitrile based on the total weight of said reaction mixture. Such a slow addition of acrylonitrile helps prevent the formation of undesirable polyacrylonitrile by-products. Thus, it is preferred that the acrylonitrile be contacted with the hydroxy compound in a dropwise or incremental fashion. The reaction may be conducted at atmospheric pressure or under super atmospheric pressure if desired. Completion of the reaction process of this invention can be determined by conventional infrared analysis on samples of the reaction product. For instance, complete reaction is indicated by a loss in the hydroxy (OH) band intensity appearing at about 3440 $cm^{-1}$; the disappearance of the cyano (CN) stretching frequency of acrylonitrile appearing at about 2220 $cm^{-1}$; and the appearance of a cyano (CN) stretching frequency of the cyanoethylated product appearing at about 2250 $cm^{-1}$. Upon completion of the reaction the catalyst employed can be neutralized by any conventional method and the desired betacyanoethyl capped hydroxy compound product obtained recovered in any conventional manner such as by stripping out any excess arylonitrile if desired and filtering the desired liquid cyanoethylated reaction product from the neutralized catalyst. Said catalysts are easily neutralized by the addition of any suitable acid, such as phosphoric acid and the like. Moreover, it is generally preferred to employ about 1 mole of a polybasic acid such as phosphoric acid, for each 1.5 moles of catalyst to be neutralized so as to allow a margin of safety in the event of over or under neutralization. Preferably the catalyst is neutralized so that a separate sample of the resulting reaction mixture has a pH of about 6.0 to about 7.0 when diluted to about a 10 percent concentration in water.

The beta-cyanoethyl capped hydroxy compounds produced by the process of this invention are very useful as starting materials for the production of many useful derivatives. For instance, when hydrolyzed in the presence of alcohols the cyanoethylated products yield corresponding esters; by catalytic hydrogenation the corresponding primary and secondary amines of the cyanoethylated products can be formed; and by platinum catalyzed hydrosilylation of a terminal olefin of an oxyalkylene nitrile product, silicon-oxyalkylene nitrile compounds can be obtained. Moreover, the beta-cyanoethyl capped hydroxy compounds and/or their derivatives have a number of widely diversified uses, for example, as wetting agents, emulsifying agents, anti-freeze agents, high boiling solvents, plasticizers, fly spray ingredients, as agents useful in the textile and leather industries, and the like.

The process of this invention is especially unique and represents a clear advancement in the art in that it affords a cyanoethylation method for directly preparing beta-cyanoethyl capped hydroxy compounds that are essentially free of polyacrylonitrile by-products (i.e. cyanoethylated products having a polyacrylonitrile absorbance (optical density) at about 298 m$\mu$± 5 of less than about 0.2). As pointed out above, this is especially important when it is desired to employ the cyanoethylated products to produce derivatives, such as primary and secondary amines, and silicon-oxyalkylene nitrile compounds, which require the use of nobel metal catalysts that can be poisoned by the polyacrylonitrile by-products in the beta-cyanoethyl capped hydroxy compound starting material. For example, it has been found by separate routine experimentation that the maximum absorbance in the absorption spectra of polyacrylonitrile appears at a wave length of about 298 m$\mu$ ± 5. Thus, measuring the polyacrylonitrile absorbance of a cyanoethylated product at about 298 m$\mu$ ± 5 affords a method for determining the amount of polyacrylonitrile by-product in the cyanoethylated compound measured. The lower the polyacrylonitrile absorbance the less polyacrylonitrile by-product present in the cyanoethylated compound. The procedure involved in measuring the absorbance of a compound is well known as witnessed by "J. of Res." National Bureau of Standards, 48, No. 12, p. 414–423, June, 1952.

In addition, it has been further found that a beta-cyanoethyl capped polyether alcohol such as

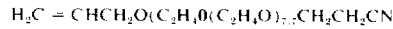

having an absorbance at about 298 m$\mu$ ± 5 of only about 0.5 contained sufficient polyacrylonitrile to poison about 50 to 100 parts per million of platinum catalyst employed in a hydrosilylation reaction of said cyanoethylated compound in an attempt to prepare the corresponding siloxane-oxyalkylene nitrile derivative of same. On the other hand, the same betacyanoethyl capped polyether alcohol when prepared according to the process of the instant invention had a polyacrylonitrile absorbance at about 298 m$\mu$ ± 5 of less than about 0.2 and was easily hydrosilylated in the presence of about 30 parts per million of platinum catalyst to its corresponding siloxane-oxyalkylene nitrile derivative.

The following examples are illustrative of the present invention and are not to be regarded as limitative. It is to be understood that all parts, percentages and proportions referred to herein and in the appended claims are by weight unless otherwise indicated. The polyacrylonitrile absorbance values given in the following examples were all measured on one percent solution samples in isopropanol at about 298 m$\mu$ ± 5; the lower the absorbance the less polyacrylonitrile by-product present in the cyanoethylated compound.

EXAMPLE 1

A beta-cyanoethyl capped polyether alcohol was prepared by adding sufficient concentrated phosphoric acid to a polyether of the formula [$H_2C = CHCH_2O(C_2H_4O)_{7.7}H$] containing about 981 ppm of potassium as the alkoxide of the polyether to produce the insitu formation of a catalyst of the potassium salts of the phosphate esters and so that a separate sample of the resulting solution of ingredients had an aqueous pH of about 10.5 when diluted to about 10 percent concentration in water. About 300 grams of the said resulting solution of ingredients were charged to a 500 cc three-necked flask along with about 0.9 grams of distilled water. The flask was fitted with a Dean-Stark trap, Friedrick condenser, thermometer and nitrogen purge line. Also attached was a constant-pressure addition funnel containing about 42.2 grams of acrylonitrile. The acrylonitrile was charged to the flask dropwise at a pot temperature between about 10°C. and about 21°C. Infrared scans on a sample of the flask contents showed when the reaction was complete as indicated by a loss in the OH band intensity, the disappearance of the CN stretching frequency of acrylonitrile and the appearance of a CN stretching frequency of the cyanoethylated product. The catalyst was then neutralized with 0.3 grams of concentrated phosphoric acid. The reaction product was then treated with 1 percent activated carbon and filtered. Then 15 grams of toluene were added to facilitate removal of excess acrylonitrile and water and the product vacuum stripped to yield the desired cyanoethylated, $CH_2 = CHCH_2O(C_2H_4O)_{7.7}C_2H_4CN$ product.

The reaction was repeated four more times with small variations in reaction times and phosphate ester catalyst concentrations, and the pertinent properties of the reaction products are listed in the following Table:

TABLE 1

| Exp. No. | PPM Phosphorus Present in Product[1] | Reaction Time[2](Min) | Polyacrylonitrile Absorbance | Percent Yield[3] |
|---|---|---|---|---|
| 1 | 170 | 280 | 0.07 | 90.7 |
| 2 | 170 | 280 | 0.08 | 90.5 |
| 3 | 175 | 75 | 0.10 | 90.3 |
| 4 | 130 | 240 | 0.06 | 94.5 |
| 5 | 130 | 215 | 0.08 | 96.0 |

[1] The amount of phosphorus present in the reaction product indicates the amount of phosphorus present during cyanoethylation. The above data shows that the catalyst was indeed the potassium salts of the phosphate ester.
[2] Reaction time indicates the time in minutes it took for completion of the reaction after all of the acrylonitrile had been added.
[3] Percent yield indicates the efficiency of the cyanoethylation process as determined by the hydroxy content found in the reaction product.

EXAMPLE 2

The following experiments represent conventional cyanoethylation with a strong base catalyst which lies outside the scope of this invention.

A beta-cyanoethyl capped polyether alcohol was prepared by adding a sufficient amount of a 50 percent aqueous solution of potassium hydroxide to a polyether having the formula $H_2C = CHCH_2O(C_2H_4O)_{7.7}H$ so that a separate sample of the resulting solution had an aqueous pH of about 10.5 when diluted to about 10 percent concentration in water. About 300 grams of the above catalyzed polyether solution was then charged to a 500 cc. three-necked flask. Attached to the flask was a constant-pressure addition funnel containing about 45.2 grams of acrylonitrile. The flask was also fitted with a Dean-Stark trap, Friedrick condenser, thermometer and nitrogen purge lines. Acrylonitrile was added to the flask dropwise at a pot temperature between 10°C. and 17°C. About 0.4 percent by weight of water based on the amount of polyether alcohol was present during cyanoethylation. Infrared scans on samples of the flask contents were taken as described in Example 1 until complete reaction was noted. The catalyst was then neutralized with about 0.3 grams of concentrated phosphoric acid, the reaction product was treated with 1 percent activated carbon for three hours and filtered to yield the desired cyanoethylated reaction product, $H_2C = CHCH_2O(C_2H_4O)_{7.7}C_2H_4CN$.

The experiment was then repeated and the pertinent properties of the reaction products are listed in the following Table:

TABLE 2

| Exp. No. | PPM Phosphorus Present in Product[1] | Polyacrylonitrile Absorbance | Percent Reaction Completion[2] |
|---|---|---|---|
| 1 | 2 | 0.58 | 97.4 |
| 2 | 2 | 0.55 | 97.7 |

[1]The amount of phosphorus present in the reaction product indicates the amount of phosphorus present during cyanoethylation. The above data shows that the catalyst was indeed potassium hydroxide.
[2]The percent reaction completion indicates the efficiency of the cyanoethylation process as determined by the hydroxy content found in the reaction product.

EXAMPLE 3

To an eight ounce bottle was charged: about 125.2 grams of deionized polyether, [$H_2C = CHCH_2O(C_2H_4O)_{7.7}H$]; about 0.06 grams of an alkyl mercaptan, [$CH_3(CH_2)_7SH$] having a 98 percent purity and about 0.04 grams of a 50 percent aqueous sodium hydroxide solution, which resulted in the insitu formation of the sodium merceptan salt catalyst; [$NaS(CH_2)_7CH_3$]. A separate sample of the resulting solution of said ingredients had an aqueous pH of about 9.7 when diluted to about 10 percent concentration in water. About 100 grams of the said resulting solution of ingredients were charged to a 250 cc. three-necked flask, fitted with a Dean-Stark trap, Friedrick condenser, thermometer and nitrogen purge line. Also attached was a constant-pressure addition funnel containing about 14.7 grams of acrylonitrile. The acrylonitrile was added to the flask dropwise at a pot temperature of about 27°C. to 32°C. After 10 minutes infrared scan of a sample of the flask contents showed a low concentration of —$OC_2H_4CN$ units. An additional charge of a slurry consisting of about 0.083 grams of $NaS(CH_2)_7CH_3$ catalyst and about 0.017 grams of water was added to the reaction mixture. The temperature of the flask contents increased to 49°C. A separate sample of the resulting solution of ingredients at this time had an aqueous pH of about 10.1 when diluted to about 10 percent concentration in water. An infrared scan of a sample of the flask contents taken 17 minutes after the additional catalyst was charged showed that the cyanoethylation reaction was complete. The $CH_3(CH_2)_7SNa$ catalyst was then neutralized with 1 drop of concentrated phosphoric acid, to yield the desired cyanoethylated $H_2C = CHCH_2O(C_2H_4O)_{7.7}C_2H_4CN$ product. The reaction product had a hydroxy content of about 0.38 percent indicating a 90.3% yield (cyanoethylation efficiency) and had a polyacrylonitrile absorbance of 0.08. Thus little, if any, polyacrylonitrile was produced.

EXAMPLE 4

To an eight ounce bottle was charged: about 0.24 grams of dodecylsuccinic anhydride; about 127.2 grams of deionized polyether, [$H_2C = CHCH_2O(C_2H_4O)_{7.7}H$]; and about 0.21 grams of about a 50.1 percent aqueous sodium hydroxide solution, which resulted in the insitu formation of the sodium salt catalyst [$CH_3(CH_2)_{11}O_2C(CH_2)CO_2Na$]. The resulting solution of ingredients contained about 0.11 percent by weight of water and a separate sample of the resulting solution of said ingredients had an aqueous pH of about 10.1 when diluted to about 10 percent concentration in water. About 100 grams of the said resulting solution of ingredients were charged to a 250 cc three necked flask, fitted with a Dean-Stark trap, Friedrick condenser, thermometer and nitrogen purge line. Also attached was a constant-pressure addition funnel containing about 14.7 grams of acrylonitrile. The acrylonitrile was added to the flask dropwise at a pot temperature of about 27°C to 36°C. The pot temperature increased to about 46°C. after acrylonitrile addition was complete. An infrared scan of a sample of the flask contents taken 10 minutes after the final addition of acrylonitrile showed that the cyanoethylation was complete. The $CH_3(CH_2)_{11}O_2C(CH_2)_2CO_2Na$ catalyst was then neutralized with one drop of concentrated phosphoric acid to yield the desired cyanoethylated, $H_2C = CHCH_2\ O(C_2H_4O)_{7.7}C_2H_4CN$ product. The reaction product had a hydroxy content of about 0.49 percent indicating an 87.5% yield (cyanoethylation efficiency) and had a polyacrylonitrile absorbance of 0.04. Thus essentially no polyacrylonitrile was formed.

EXAMPLE 5

To an eight ounce bottle was charged: about 0.54 grams of a mixed phosphate ester of $RPO(OH)_2$ and $R_2P(O)OH$ where R is a $CH_2 = CHCH_2O(C_2H_4O)_{7.7}$ radical; about 104.8 grams of allyl alcohol and about a 50 percent aqueous potassium hydroxide solution which resulted in the insitu formation of the potassium salt catalyst of said phosphates. The resulting solution of ingredients had an aqueous pH of about 10.5 when diluted to about 10 percent concentration in water. About 58.0 grams of the said resulting solution of ingredients were charged to a 250 cc three-necked round bottom flask, fitted with a Dean-Stark trap, Friedrick condenser, thermometer and nitrogen purge line. Also attached was a constant-pressure addition funnel containing about 55.7 grams of acrylonitrile. The acrylonitrile was added to the flask dropwise at a pot temperature of between 24°C. and 51°C. An infrared scan of a sample of the flask contents taken 28 minutes after the final addition of acrylonitrile showed that the cyanoethylation was complete. The catalyst was then neutralized with two drops of concentrated $H_3PO_4$ to yield the desired cyanoethylated, $H_2C = CH—CH_2O(C_2H_4)_{7.7}C_2H_4CN$ product. The reaction product had a hydroxy content of about 2.0 percent indicating a 85.9% yield (cyanoethylation efficiency) and had a polyacrylonitrile absorbance of 0.04. Thus, essentially no polyacrylonitrile was formed.

EXAMPLE 6

To an eight ounce bottle was charged: about 0.84 grams of phosphate ester mixture as described in Example 5 about 152.7 grams of isopropanol and about 0.35 grams of about a 50.2 percent aqueous potassium hydroxide solution, which resulted in the insitu formation of the potassium salt catalyst of said phosphates. The resulting solution of said ingredients had an aqueous pH of about 10.5 when a separate sample was diluted to about 10 percent concentration in water. About 70.0 grams of the said resulting solution of ingredients were charged to a 250 cc three-necked round bottom flask, fitted with a Dean-Stark trap, Friedrick condenser, thermometer and nitrogen purge line. Also attached was a constant-pressure addition funnel containing about 64.9 grams of acrylonitrile. The acrylonitrile was added to the flask dropwise at a pot-temperature of about 29°C. to 49°C. An infrared scan of a sample of the flask contents taken 9 minutes after the final addition of acrylonitrile showed that the cyanoethylation was complete. The catalyst was then neutralized with three drops of concentrated H₃PO₄, to yield the amount of desired cyanoethylated product. The reaction product

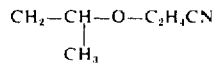

had a hydroxy content of about 1.4 percent indicating a 90.5% yield (cyanoethylation efficiency) and had a polyacrylonitrile absorbance of 0.15. Thus, little if any, polyacrylonitrile was formed.

EXAMPLE 7

Four cyanoethylated alcohol products were hydrosilylated in the same manner using the same amounts and conditions with a siloxane polymer having the average formula (CH₃)₃SiO[(CH₃)₂SiO]₅(MeHSiO)₇Si(CH₃)₃ in the presence of 30 percent by weight of toluene using chloroplatinic acid as the catalyst.

The four cyanoethylated starting materials were (A) distilled allyloxyethylcyanide, [CH₂ = CHCH₂OC₂H₄CN] having a polyacrylonitrile absorbance of 0.01; (B) a cyanoethylated polyether [CH₂ = CHCH₂O(C₂H₄O)₇.₇C₂H₄CN] prepared in the same manner as described in Example 1 and having a polyacrylonitrile absorbance of 0.07; (C) a cyanoethylated polyether [CH₂ = CHCH₂O(C₂H₄O)₇.₇C₂H₄CN] also prepared in the same manner as described in Example 1 and having a polyacrylonitrile absorbance of 0.10; and (D) a cyanoethylated polyether [CH₂ = CHCH₂O(C₂H₄O)₇.₇C₂H₄CN] prepared using potassium hydroxide as the catalyst as described in Example 2 and having a polyacrylonitrile absorbance of 0.56.

The hydrosilylation reactions were run at about 90° ± 5°C. in a 250 cc three-necked flask, fitted with a Dean-Stark trap, Friedrick condenser, thermometer and nitrogen purge line. The reactions were considered complete when the silanic hydrogen content was no longer detectable. The following order of reactivity was observed in the four hydrosilylation reactions.

A. With the allyloxyethylcyanide starting material having a polyacrylonitrile absorbance of 0.01 the hydrosilylation reaction was complete in about 30 minutes with about 30 ppm platinum catalyst.

B. With the cyanoethylated polyether having a polyacrylonitrile absorbance of 0.07 the hydrosilylation reaction went to completion in about 3 hours with about 30 ppm platinum catalyst.

C. With the cyanoethylated polyether having a polyacrylonitrile absorbance of 0.10, the hydrosilylation reaction went to completion in about 3 hours with 30 ppm platinum catalyst.

D. With the cyanoethylated polyether having a polyacrylonitrile absorbance of 0.56, the reaction had to be recatalyzed several times and required about 125 ppm platinum catalyst over a 5 hour period to drive the reaction to completion.

The above data shows a clear correlation between polyacrylonitrile absorbance at about 298 ± 5 mμ and the extent of platinum poisoning.

Various modifications in variations of this invention are obvious to a worker skilled in the art and it is understood that such modifications in variation are to be included within the purview of this application in the spirit and scope of the appended claims.

What is claimed is:

1. A cyanoethylation process for preparing betacyanoethyl capped hydroxy compounds that are essentially free of polyacrylonitrile by-products, said compounds having the general formula

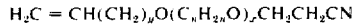

wherein y has a value of 0 to 4 inclusive, n has a value of 2 to 4 inclusive and x has a value of 1 to 20; said process comprising reacting at a temperature of 0° to 80°C. an unsaturated polyether alcohol having the general formula

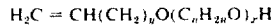

wherein n, y and x are the same as defined above, with acrylonitrile in the presence of water and a catalyst which is an alkali metal or tetraalkyl ammonium salt of an acid selected from the class consisting of partial phosphate esters, alkyl mercaptans, cresols and partial pyrophosphate esters, by (A) slowly adding said acrylonitrile to a mixture containing said alcohol, water and catalyst, (B) neutralizing said catalyst and recovering the beta-cyanoethyl capped hydroxy compound product; wherein;
  a. said catalyst is soluble in said mixture of alcohol, water and catalyst ingredients;
  b. said acid has an aqueous pKa value of greater than 10 but less than 15;
  c. the amount of catalyst employed is such that the aqueous pH of a separate mixture containing about 10 percent by weight of a sample of said mixture of alcohol, water and catalyst ingredients and about 90 percent by weight of additional water ranges from 9 to about 10.7;
  d. the amount of acrylonitrile employed ranges from about 1 to about 1.1 moles for every hydroxy group on said alcohol to be reacted;
  e. the rate of contact between the alcohol and acrylonitrile reactants is such that the reaction mixture of alcohol, water, catalyst, and acrylonitrile never contains more than 5 percent by weight of unreacted acrylonitrile based on the total weight of said reaction mixture;
  f. the amount of water employed ranges from about 0.1 to about 0.5 percent by weight based on the amount of said alcohol employed.

2. A process as defined in claim 1 wherein y has a value of 1.

3. A process as defined in claim 1, wherein the catalyst is a salt of a partial phosphate ester having the general formula

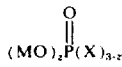

wherein M is an alkali metal or tetraalkyl ammonium radical; z has a value of 1 to 2 inclusive; and X is an alkoxy radical or a polyether radical of the formula —(OC$_n$H$_{2n}$)$_x$OR wherein R is a monovalent hydrocarbon radical, x has a value of 1 to 20 and n has a value of 2 to 4 inclusive.

4. A process as defined in claim 1, wherein the catalyst is a salt of a partial phosphate ester having the general formula

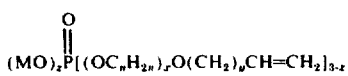

werein M is an alkali metal selected from the group consisting of sodium and potassium; $z$ has a value of 1 to 2 inclusive; $x$ has a value of 1 to 20; $y$ has a value of 0 to 4 inclusive; and $n$ has a value of 2 to 4 inclusive.

5. A process as defined in claim 4, wherein the reaction temperature is about 15°C. to 60°C.; wherein $y$ has a value of 1; and wherein the amount of water employed is about 0.3 weight percent based on the amount of said hydroxy compound employed.

* * * * *

UNITED STATES PATENT OFFICE
CERTIFICATE OF CORRECTION

Patent No. 3,957,848                     Dated May 18, 1976

Inventor(s) James D. Reedy et al

It is certified that error appears in the above-identified patent and that said Letters Patent are hereby corrected as shown below:

Column 1, line 5, "cyanothylation" should be ---cyanoethylation---.

Column 1, line 29, "byproduct" should be ---by-product---.

Column 4, line 34, "Acedemic" should be ---Academic---.

Column 5, line 53, "resuls" should be ---results---.

Column 5, line 57, "likely" should be ---likeli---.

Column 7, line 56; column 9, lines 21 and 60 and column 10, lines 25 and 53, in each occurrance the term "insitu" should be ---in situ---.

Column 11, line 5 that part of the formula shown as "$CH_2$-" should be ---$CH_3$---.

Claim 4, column 13, line 5, "werein" should be ---wherein---.

*Signed and Sealed this*

Twenty-eighth *Day of* December 1976

[SEAL]

*Attest:*

RUTH C. MASON
*Attesting Officer*

C. MARSHALL DANN
*Commissioner of Patents and Trademarks*